(12) United States Patent
Beymer et al.

(10) Patent No.: US 9,274,598 B2
(45) Date of Patent: Mar. 1, 2016

(54) SYSTEM AND METHOD FOR SELECTING AND ACTIVATING A TARGET OBJECT USING A COMBINATION OF EYE GAZE AND KEY PRESSES

(75) Inventors: David Beymer, San Jose, CA (US); Stephen P. Farrell, San Francisco, CA (US); Shumin Zhai, San Jose, CA (US)

(73) Assignee: International Business Machines Corporation, Armonk, NY (US)

( * ) Notice: Subject to any disclaimer, the term of this patent is extended or adjusted under 35 U.S.C. 154(b) by 2959 days.

(21) Appl. No.: 10/835,483

(22) Filed: Apr. 29, 2004

(65) Prior Publication Data

US 2005/0243054 A1   Nov. 3, 2005

(51) Int. Cl.
   G06F 3/048   (2013.01)
   G06F 3/01    (2006.01)
   A61B 3/00    (2006.01)
   A61B 3/113   (2006.01)

(52) U.S. Cl.
   CPC .............. G06F 3/013 (2013.01); A61B 3/0033 (2013.01); G06F 3/014 (2013.01); *A61B 3/113* (2013.01)

(58) Field of Classification Search
   CPC ... G06F 3/0482; G06F 3/011; G06F 3/04812; G06F 3/013; G06F 3/014; A61B 3/0033; A61B 3/113
   USPC .......... 700/701–703; 345/173, 156, 178, 157; 715/764, 856, 773
   See application file for complete search history.

(56) References Cited

U.S. PATENT DOCUMENTS

| | | | |
|---|---|---|---|
| 4,595,990 A * | 6/1986 | Garwin et al. | ................ 708/141 |
| 4,836,670 A | 6/1989 | Hutchinson | |
| 4,950,069 A | 8/1990 | Hutchinson | |
| 5,388,199 A | 2/1995 | Kakazu et al. | |
| 5,471,542 A | 11/1995 | Ragland | |
| 5,546,472 A | 8/1996 | Levin | |
| 5,638,176 A | 6/1997 | Hobbs et al. | |
| 5,731,805 A | 3/1998 | Tognazzini et al. | |
| 5,786,815 A | 7/1998 | Ford | |
| 5,808,601 A | 9/1998 | Leah et al. | |
| 5,822,599 A | 10/1998 | Kidder et al. | |

(Continued)

FOREIGN PATENT DOCUMENTS

TW     372301     10/1999

OTHER PUBLICATIONS

Findlay, John M., "Saccade Target Selection During Visual Search", Vision Research vol. 37 Issue 5, Mar. 1997.*

(Continued)

*Primary Examiner* — Steven Sax
*Assistant Examiner* — Christopher J Fibbi
(74) *Attorney, Agent, or Firm* — Fleit Gibbons Gutman Bongini & Bianco PL; Thomas Grzesik

(57) ABSTRACT

A pointing method uses eye-gaze as an implicit control channel. A user looks in a natural fashion at a target object as a button on a graphical user interface and then presses a manual selection key. Once the selection key is pressed, the present method uses probability analysis to determine a most probable target object and to highlight it. If the highlighted object is the target object, the user can select it by pressing a key such as the selection key once again. If the highlighted object is not the target object, the user can select another target object using additional keys to navigate to the intended target object.

39 Claims, 14 Drawing Sheets

(56) References Cited

U.S. PATENT DOCUMENTS

| | | | |
|---|---|---|---|
| 5,835,083 A | | 11/1998 | Nielsen et al. |
| 5,839,000 A | | 11/1998 | Davis, Jr. et al. |
| 5,850,211 A | | 12/1998 | Tognazzini |
| 5,886,683 A | * | 3/1999 | Tognazzini et al. ............ 715/700 |
| 5,898,423 A | | 4/1999 | Tognazzini et al. |
| 5,912,721 A | | 6/1999 | Yamaguchi et al. |
| 6,067,069 A | | 5/2000 | Krause |
| 6,067,079 A | * | 5/2000 | Shieh ............................ 345/173 |
| 6,152,563 A | | 11/2000 | Hutchinson et al. |
| 6,182,098 B1 | * | 1/2001 | Selker ............................ 715/526 |
| 6,204,828 B1 | * | 3/2001 | Amir et al. ........................ 345/7 |
| 6,243,076 B1 | | 6/2001 | Hatfield |
| 6,299,308 B1 | | 10/2001 | Voronka et al. ............... 351/210 |
| 6,323,884 B1 | * | 11/2001 | Bird et al. ...................... 715/810 |
| 6,377,284 B1 | | 4/2002 | Lentz et al. |
| 6,393,136 B1 | | 5/2002 | Amir et al. .................... 382/103 |
| 6,438,752 B1 | * | 8/2002 | McClard ......................... 725/46 |
| 6,456,262 B1 | * | 9/2002 | Bell .................................. 345/8 |
| 6,466,250 B1 | | 10/2002 | Hein et al. ....................... 348/14 |
| 6,577,329 B1 | * | 6/2003 | Flickner et al. ............... 715/774 |
| 6,594,687 B1 | | 7/2003 | Yap et al. |
| 6,603,491 B2 | | 8/2003 | Lemelson et al. |
| 6,608,615 B1 | * | 8/2003 | Martins ......................... 345/156 |
| 6,637,883 B1 | * | 10/2003 | Tengshe et al. ............... 351/210 |
| 6,659,611 B2 | | 12/2003 | Amir et al. .................... 351/210 |
| 6,873,314 B1 | * | 3/2005 | Campbell ...................... 345/156 |
| 6,876,397 B2 | | 4/2005 | Funakoshi et al. |
| 6,956,979 B2 | | 10/2005 | Janakiraman et al. |
| 7,013,258 B1 | * | 3/2006 | Su et al. ............................ 704/1 |
| 7,023,428 B2 | * | 4/2006 | Pihlaja .......................... 345/173 |
| 7,027,655 B2 | * | 4/2006 | Keeney et al. ................ 382/239 |
| 7,029,121 B2 | * | 4/2006 | Edwards ....................... 351/246 |
| 7,120,880 B1 | * | 10/2006 | Dryer et al. ................... 715/863 |
| 7,530,031 B2 | * | 5/2009 | Iwamura et al. .............. 715/864 |
| 7,664,649 B2 | * | 2/2010 | Jost et al. ...................... 704/275 |
| 2002/0154169 A1 | | 10/2002 | Talley et al. |
| 2003/0016332 A1 | | 1/2003 | Trajkovic et al. |
| 2004/0156020 A1 | * | 8/2004 | Edwards ....................... 351/209 |
| 2006/0259345 A1 | * | 11/2006 | Stetina ............................ 705/10 |

OTHER PUBLICATIONS

Search Report for Taiwan Patent Application No. 094111622 received Aug. 9, 2010.

John Hansen et al., "Language Technology in a Predictive, Restricted On-screen Keyboard with Ambiguous Layout for Severely Disabled People," available at: http://www.it-c.dk/research/EyeGazeInteraction/Papers/Hansen_et_al_2003a.pdf, on Apr. 28, 2004.

Shumin Zhai, "Two Handed and Gaze Input," Stanford and Princeton Lecture, Nov. 29, 1999.

Matthew Garrett et al., "Implementation of Dasher, an information efficient, input mechanism," May 23, 2003.

Dario Salvucci, "An Interactive Model-Based Environment for Eye-Movement Protocol Analysis and Visualization," In Proceedings of the Eye Tracking Research and Applications Symposium (pp. 57-63), 2000.

Samah Ramadan et al., "Eye Tracking using Active Deformable Models," The III Indian Conference on Computer Vision, Graphics and Image Processing, India, Dec. 2002.

Eric Horvitz et al., "Models of Attention in Computing and Communication: From Principles to Applications," available at: http://research.microsoft.com/~horvitz/cacm-attention.pdf, on Jan. 24, 2004.

Gamhewage De Silva et al., "Human Factors Evaluation of a Vision-Based Facial Gesture Interface," available at: http://www.mis.atr.co.jp/~mlyons/pub_pdf/lyons_cvprhci.pdf, on Apr. 28, 2004.

Andre Bergeron et al., "Superior colliculus encodes distance to target, not saccade amplitude, in multi-step gaze shifts," Nature Neuroscience, vol. 6, No. 4, Apr. 2003.

Justin Gardner et al., "Linked Target Selection for Saccadic and Smooth Pursuit Eye Movements," The Journal of Neuroscience, Mar. 15, 2001, 21(6):2075-2084.

Jingtao Wang et al., "Chinese Input with Keyboard and Eye-Tracking—An Anatomical Study," CHI 2001 (Mar. 31-Apr. 5).

Gregory Horwitz et al., "Target Selection for Saccadic Eye Movements: Direction-Selective Visual Respnses in the Superior Colliculus," The American Physiological Society, J. Neurophysiol., vol. 86, Nov. 2001.

Francesco Maringelli et al., "Shifting visuo-spatial attention in a virtual three-dimensional space," 2001 Elsevier Science B.V.

D.W.J. Cabel et al., "Control of saccade initiation in a countermanding task using visual and auditory stop signals," Exp Brain Res (2000) 133:431-441.

Sumin Zhai, "What's in the Eyes for Attentive Input," Communications of the ACM, vol. 46, No. 3, Mar. 2003.

Narcisse P. Bichot et al., "Effects of similarity and history on neural mechanisms of visual selection," Nature Neuroscience, vol. 2, No. 6, Jun. 1999, pp. 549-554.

Ashmore, M., et al., "Efficient Eye Pointing with a Fisheye Lens," May 7, 2005, pp. 1-8.

Zhai, S., et al., "Human On-line Response to Target Expansion," Pointing and Manipulation, Apr. 5-10, 2003, pp. 1-8. vol. 5, Issue 1.

McGuffin, M., et al., "Acquisition of Expanding Targets," Apr. 20-25, 2002, pp. 1-8.

John, B., et al., "The GOMS Family of User Interface Analysis Techniques: Comparison and Contrast," Dec. 1996, pp. 320-351, vol. 3, No. 4.

Bederson, B., et al., "Pad++: A Zoomable Graphical Interface System," Conference on Human Factors in Computing Systems, May 7-11, 1995, pp. 1-4.

Furnas, G., "Generalized Fisheye Views," Human Factors in Computing Systems, Apr. 1986, pp. 1-8.

Bederson, B., et al., "Pad++: A Zooming Graphical Interface for Exploring Alternate Interface Physics," ACM Symposium on User Interface Software and Technology, Nov. 1994, pp. 1-10.

Zhai., S., at al "Manual and Gaze Input Cascaded (MAGIC) Pointing," ACM Conference on Human Factors in Computing Systems, May 15-20, 1999, pp. 1-8.

\* cited by examiner

How Do We Reach You?

700

First Name: _____
Last Name: _____
Age Range: _____ ▶ "Click" Arrow for Choices
Street Address: _____
_____ 705
_____
City: _____
State or Canadian Province: ▶ "Click" Arrow for Choices 710
Country: ▶ "Click" Arrow for Choices
Zip Code or Postal Code: _____
E-Mail Address: _____
Home Phone: (___) ___ (Area Code)(Phone Number)
(Numbers Only)
Work Phone: (___) ___ Ext. ___ (Area Code)(Phone Number)(Extension)
(Numbers Only)

*FIG. 7*

SYSTEM AND METHOD FOR SELECTING AND ACTIVATING A TARGET OBJECT USING A COMBINATION OF EYE GAZE AND KEY PRESSES

CROSS-REFERENCE TO RELATED APPLICATION

The present patent application is related to co-pending U.S. patent application Ser. No. 10/648,120, filed on Aug. 25, 2003, titled "System and Method for Selectively Expanding or Contracting a Portion of a Display Using Eye-Gaze Tracking," which is incorporated herein by reference.

FIELD OF THE INVENTION

The present invention generally relates to gaze tracking systems and interactive graphical user interfaces. Particularly, the present invention relates to a system for selecting a graphical object from a portion of a video screen based on the coincidence of eye-gaze and selection key navigation among candidate targets using one or more navigation keys, and activation of a target using an activation key. More specifically, the present invention provides a number of interaction techniques for situations when gaze information is not specific and the intended target is ambiguous. Imprecision can also be reduced by using a probabilistic model possibly comprising the geometry, application state, eye movements subsequent to object highlighting, or object history.

BACKGROUND OF THE INVENTION

In human-computer interaction, one of the most basic elements involves selecting and activating a target object using a pointing device. Target object activation and selection are involved in opening a file with a mouse "click", following a world wide web link, choosing a menu item, redefining a typing or drawing insertion position, and other such operations. Selection and activation are two stages of interaction. Selection refers to the stage where an object is chosen, and activation refers to invoking the function of the object. Engineers and scientists have developed many different approaches to target object interaction. One of the most popular target object interaction devices is the computer mouse. Although computer mice are practically essential with today's computers, intense use can be fatiguing and time consuming. Further, the use of a mouse is difficult for handicapped users or users with limited hand mobility due to, for example, carpal tunnel syndrome or arthritis.

Despite these limitations, further improvement of mouse-based target object selection and activation systems has been difficult. One interesting idea for possible improvement uses eye gaze tracking instead of mouse input. There are several known techniques for monitoring eye gaze. One approach senses the electrical impulses of eye muscles to determine eye gaze. Another approach magnetically senses the position of special user-worn contact lenses having tiny magnetic coils. Still another technique, called "corneal reflection", calculates eye gaze by projecting an invisible beam of light toward the eye, and monitoring the angular difference between pupil position and reflection of the light beam.

With these types of gaze tracking systems, the cursor is positioned on a video screen according to the calculated gaze of the computer operator. A number of different techniques have been developed to select and activate a target object in these systems. In one example, the system activates a target object when it detects the operator fixating at the target object for a certain time. Another way to activate a target object is when the operator's eye blinks.

One problem with these systems is that humans use their eyes naturally as perceptive, not manipulative, body parts. Eye movement is often outside conscious thought, and it can be stressful to carefully guide eye movement as required to accurately use these target object activation systems. For many operators, controlling blinking or staring can be difficult, and may lead to inadvertent and erroneous target object selection. Thus, although eye gaze is theoretically faster than any other body part, the need to use unnatural activation (e.g., by blinking or staring) limits the speed advantage of gaze controlled pointing over manual pointing.

Another limitation of the foregoing systems is the difficulty in making accurate and reliable eye tracking systems. Because of eye jitter and other inherent difficulties in precisely monitoring eye gaze, only relatively large target objects can be activated by gaze-controlled pointing techniques. One approach to solving these problems is to use the current position of the gaze to set an initial display position for the cursor (reference is made, for example, to U.S. Pat. No. 6,204,828).

The cursor is set to this initial position just as the operator starts to move the pointing device. The effect for this operation is that the mouse pointer instantly appears where the operator is looking when the operator begins to move the mouse. Since the operator needs to look at the target object before pointing at it, this method effectively reduces the cursor movement distance. However, activation of the object requires the use of a pointing device such as a mouse, requiring the user to move a hand from a keyboard to the mouse or otherwise disturb the natural process of using the keyboard.

Another approach to activating graphical objects with eye gaze uses the eye-gaze as an input channel without a manual input device for the entire control process. Reference is made to Salvucci, D. D., and Anderson, J. R. (2000). Intelligent Gaze-Added Interfaces. Proc. CHI 2000: ACM Conference on Human Factors in Computing Systems, pages 273-280. Activation of the target object is performed using a special key such as the "enter" key. The cursor follows the user's gaze at all times. However, this moving cursor can be distracting to the user. Furthermore eye tracking precision can not be precise enough to locate some of the small GUI objects.

In particular, conventional eye gaze systems are limited as devices for activating objects on a graphical user interface (GUI). Gaze detection is not accurate enough to reliably activate target objects (or widgets) such as small buttons on a GUI. Further, eye gaze has both voluntary and involuntary aspects, making it difficult to use eye gaze as a pointing or activation device.

What is lacking is a technique that enables computer interaction with only gaze and keyboard. There have been some approaches to do this, but they rely on users intentionally treating gaze as a pointing device, which is unnatural and distracting in practice. What is therefore needed is to enable support for keyboard interaction concurrently with a fixated gaze on, or a natural look at the target, which happens to be what people do naturally. While interaction is typically thought of as selection and then activation, by interposing a navigation stage between these, the present invention enables the user to adjust for imprecision in the gaze tracking apparatus.

SUMMARY OF THE INVENTION

The present invention satisfies this need, and presents a system, a computer program product, and an associated method (collectively referred to herein as "the system" or "the present system") for selecting and activating a target object using eye gaze and an a combination of key presses. In terms of the present invention, a gaze is a natural look that a user normally uses when interacting with a display, for example. No unnatural use of the eyes in length of gaze or blinking is required by the present system.

The present system is a pointing method using eye-gaze as an implicit control channel. A user looks in a natural fashion at a target object as a button on a graphical user interface and then presses a selection key. Once the selection key is pressed, the present system uses probability reasoning to determine a most probable target object and to highlight it. If the highlighted object is the target object, the user can select it by pressing a key such as the selection key once again. If the highlighted object is not the target object, the user can select another target object using additional keys to navigate to the intended target object.

The present system enables target object selection and activation without an analog pointing device by using gaze detection and user input on a keyboard. To resolve ambiguities that may occur, for example, when two widgets are close to each other, the present system comprises a user interface mechanism to navigate between multiple possibilities. The present system may further comprise a probabilistic model to determine which widget is more likely to be the target.

In addition, the present system can be applied to handheld devices with small keyboards such as personal digital assistants, reducing reliance on data entry with a stylus. Present data entry for devices with small virtual screens or keyboards is tedious and time consuming. Use of the present system with small virtual screens or keyboards speeds data entry, providing a more efficient and enjoyable user interface to these devices. Similarly, the present system can be applied to any device with an interactive input such as a laptop computer, a cell phone, an electronic whiteboard, televisions, an adaptive billboard, household appliances/entertainment, computer games, and similar other devices. The present method can be also applied to "intelligent environments" where multiple displays, appliances and devices can be selected and activated by the same method. Similarly, it can be applied in 3D virtual environments in which multiple virtual identities can be selected.

Most typically the present system works on a computer graphical user interface (GUI) with a gaze-tracking device. The present system operates in object space on the GUI rather than a geometry space. For example, every space on a computer screen is assigned to a GUI object (also referenced herein as a target or widget) such as a button, a menu item, a text window, or a hyperlink. A gaze-measuring device comprising, for example, one or more cameras measures a user's gaze position, the point where the user is naturally looking. The gaze position is assigned to a target according to a probabilistic reasoning model. As an advantage, operating in object space eliminates unnecessary control resolution by the present system. The present system does not have to determine the exact point at which the user is naturally looking. Rather, the present system simply determines the most probable object as implemented by the implemented model.

The gaze-tracking device of the present system is continually determining the gaze position of the user. When the user wishes to select a target object, the user presses a selection key. The target object comprises interactive buttons, text, pull down menus, hyperlinks on a web page, or any other object on a GUI that can be manipulated by the user through interaction. The selection key may be any key on a keyboard such as the enter key. Alternatively, the selection key may be a key added to the keyboard that is dedicated to the use of the present system.

In many circumstances the coincidence of gaze and keyboard press can be used to unambiguously identify a target object such as button or hyperlink. In other cases, however, there is ambiguity. The present invention provides a number of techniques for resolving ambiguity relying on further keyboard interaction, the state of the computer application, and instantaneous eye gaze changes. The latter two conditions can be used to feed a probabilistic model to rank possible targets by likelihood. This ranking can be used to choose a target, or simply to minimize keyboard interactions, for example by sorting the targets by probability rank.

When the selection key is pressed, the present system highlights an object on the GUI that is determined by the probabilistic model. If more than one object is located near the gaze position, the present system highlights the most probable object as determined from the gaze position. Highlighting the most probable object comprises darkening/lightening the object's color, placing a cursor over the object, placing a bounding box around the most probable object, or any other means of emphasizing the most probable object.

In one embodiment, the model could be a pluggable module. There are 3 possible outcomes of the probabilistic model: it identifies 0 candidate, it identifies exactly 1 candidate, it identifies more than 1 candidate. If it identifies 0, it should (perhaps) deselect the current selection; if it identifies 1, then it would highlight the candidate and let the user activate it by pressing the activation; if it identifies more than 1, then it highlights the most probable, and allows interaction to choose the correct one, possibly with the results sorted by probability, geometry or an integration of both.

If the most probable object is not the desired target object, the user may use navigation keys to highlight another object by, for example, moving the cursor (which can be a bounding box or other graphical means) to the next object. The cursor movement can be determined by the location of the navigations key pressed. For example, if a navigation key to the left is pressed, the cursor (highlight) moves to a likely object on the left of the initially highlighted object. Alternatively, the order of the movement can be ordered by the probability (N-best list) and the highlight moves down on the N-best list each time a navigation key is pressed.

The user may repeat this process until the target object is selected. The user may then press the activation key to activate the target object. In essence, the present system implicitly utilizes the eye-gaze information to reduce the uncertainty of the user's need or intention to a few possibilities whose number, or bits of information, is small enough to be resolved by key presses. In an embodiment, highlighting is removed from the probable object if the user does not press the activation key within a predetermined period of time.

The navigational keys may be any group of keys on a keyboard such as, for example, the arrow keys. Further, the navigational keys may be any group of keys or key combinations on the keyboard. The navigation keys may be grouped together, or separated. In addition, some of the navigation keys may be assigned to the right hand side of the keyboard while the activation key is assigned to the left hand side of the keyboard.

Another embodiment allows the user to retain the "home" typing position. Specifically, the keys near the right hand in the "home" position, "U", "O", "H", "J", "K", "L", "M", and "." (on a "QWERTY" keyboard), are used to navigate. This embodiment might be most appropriate for data entry technicians, or others that need to work rapidly without removing their hands from the home position. It might also reduce hand movement stress.

In one embodiment, the next most probable object is highlighted through eye-gaze techniques. When a user presses the selection key, the present system highlights the most probable object. However, eye gaze trackers are not perfect, so the most probable object may not be the true target. Typically, in these cases, the user will involuntarily shift their gaze from the intended target to the most probable target. The present system notes the shift in gaze, and automatically highlights the desired target object.

BRIEF DESCRIPTION OF THE DRAWINGS

The various features of the present invention and the manner of attaining them will be described in greater detail with reference to the following description, claims, and drawings, wherein reference numerals are reused, where appropriate, to indicate a correspondence between the referenced items, and wherein:

FIG. 7 is a diagram of an application form that illustrates the performance of the target object selection system of FIG. 1;

DETAILED DESCRIPTION OF PREFERRED EMBODIMENTS

The following definitions and explanations provide background information pertaining to the technical field of the present invention, and are intended to facilitate the understanding of the present invention without limiting its scope:

Fixation: A natural look by a user's eye at a particular object on a video screen.

Gaze Position: a point where the user is calculated to be naturally looking.

GUI (Graphical User Interface): A graphics-based user interface with pictures as well as words on a display that incorporates movable windows, icons and a mouse.

Interactive object (also called widget): An object or element that accepts input from the user through typed commands, voice commands, mouse clicks, or other means of interfacing and performs an action or function as a result of the input.

Internet: A collection of interconnected public and private computer networks that are linked together with routers by a set of standards protocols to form a global, distributed network.

Natural Look: the action of a user in employing sight in a given direction or on a given object.

Saccade: An involuntary rapid intermittent eye movement between fixations.

Target: an interactive graphical element or GUI element such as a button or a scroll bar hyperlink, or non-interactive object such as text that the user wishes to identify through a natural look.

Highlighting: Visually emphasizing one or more interactive objects.

Selecting: choosing exactly one object for activation. It may include a different form of highlighting.

Activating: Invoking the function of the interactive object, e.g., when releasing a button.

Selection Key: any used in combination with eye gaze to select an object.

Navigation Key(s): any key used to change the selection from object to another.

Activation key: any key used to trigger the function of the object.

Web browser: A software program that allows users to request and read hypertext documents. The browser gives some means of viewing the contents of web documents and of navigating from one document to another.

World Wide Web (WWW, also Web): An Internet client-server hypertext distributed information retrieval system.

Figure 1:
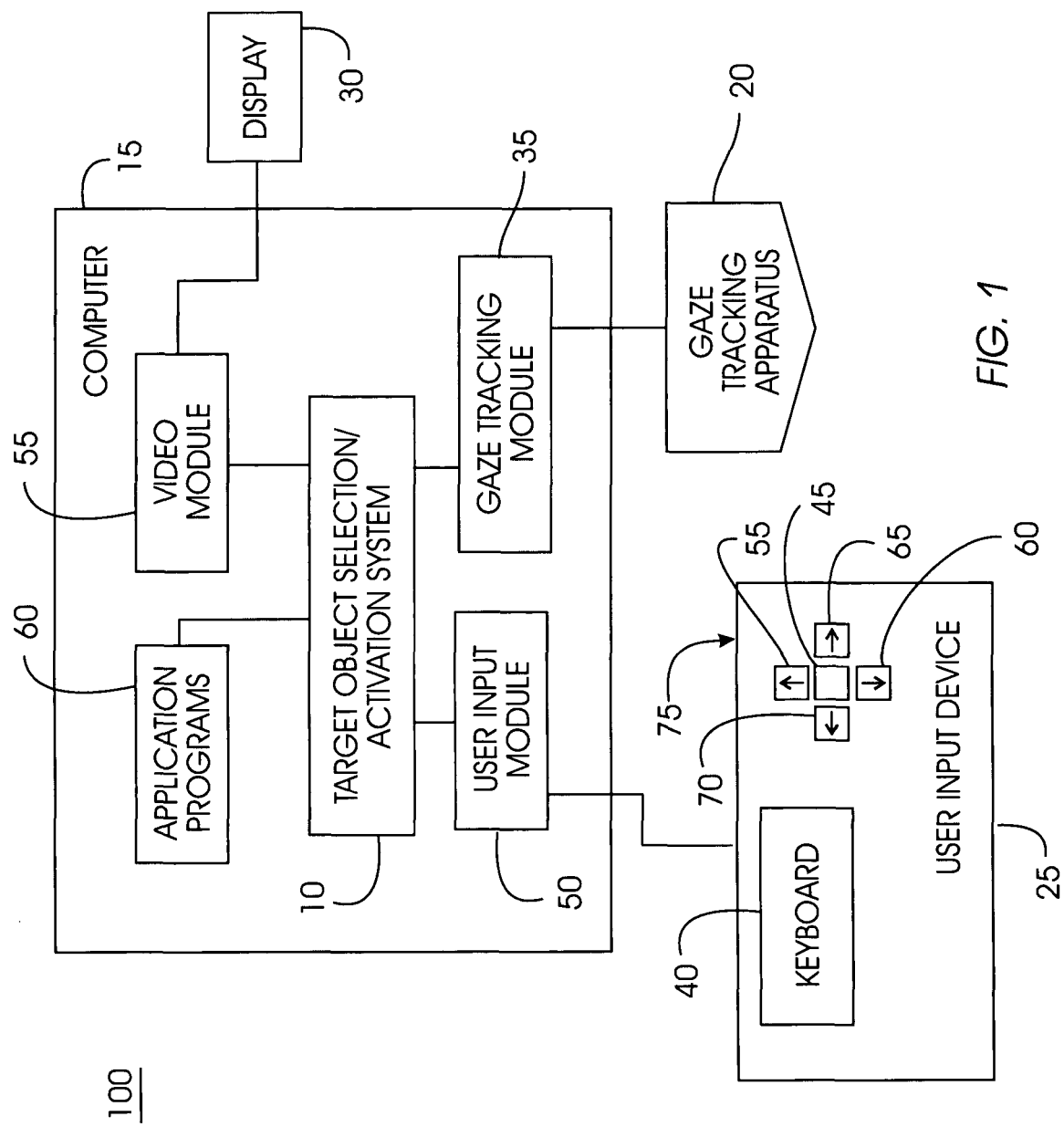
FIG. 1 is a schematic illustration of an exemplary operating environment in which a target object selection system of the present invention can be used.

FIG. 1 illustrates an exemplary high-level architecture of an integrated gaze/manual control system 100 comprising a target object selection system 10. System 10 comprises a software programming code or computer program product that is typically embedded within, or installed on a computer. Alternatively, system 10 can be saved on a suitable storage medium such as a diskette, a CD, a hard drive, or like devices.

Generally, the integrated gaze/manual control system 100 comprises a computer 15, a gaze tracking apparatus 20, a user input device 25, and a display 30. The system 100 may be used, for example, by a "user", also referred to as an "operator".

The gaze tracking apparatus 20 is a device for monitoring the natural look of the computer operator. The gaze tracking apparatus 20 may use many different known or available techniques to monitor the natural look of the user, depending upon the particular needs of the application. As one example, the gaze tracking apparatus 20 may employ one or more of the following techniques:
1. Electro-Oculography, which places skin electrodes around the eye, and records potential differences, representative of eye position.
2. Corneal Reflection, which directs an infrared light beam at the operator's eye and measures the angular difference between the operator's mobile pupil and the stationary light beam reflection.

3. Lumbus, Pupil, and Eyelid Tracking. This technique comprises scanning the eye region with an apparatus such as a television camera or other scanner, and analyzing the resultant image.
4. Contact Lens. This technique use some device attached to the eye with a specially manufactured contact lens. With the "optical lever", for example, one or more plane mirror surfaces ground on the lens reflect light from a light source to a photographic plate or photocell or quadrant detector array. Another approach uses a magnetic sensor in conjunction with contact lenses with implanted magnetic coils.

A number of different gaze tracking approaches are surveyed in the following reference: Young et al., "Methods & Designs: Survey of Eye Movement Recording Methods", Behavior Research Methods & Instrumentation, 1975, Vol. 7(5), pp. 397-429. Ordinarily skilled artisans, having the benefit of this disclosure, will also recognize a number of different devices suitable for use as the gaze tracking apparatus 20.

As a specific example of one gaze tracking approach for use in system 100, reference is made to the following patents that are incorporated herein by reference: U.S. Pat. No. 4,836,670; U.S. Pat. No. 4,950,069; and U.S. Pat. No. 4,595,990. Although the gaze tracking apparatus 20 may be a custom product, commercially available products may alternatively be used instead.

The software programming associated with the gaze tracking apparatus 20 may be included with the gaze tracking apparatus 20 itself. The specific example of FIG. 1 illustrates the associated software implemented in the gaze tracking module 35, described below. The gaze tracking module 35 may be included solely in the computer 15, in the gaze tracking apparatus 20, or in a combination of the two, depending upon the particular application.

Advantageously, the present invention is capable of operation with different eye-tacking accuracy. If it is a high accuracy system, none or few navigation key presses would be needed to reach the target. If it is an inexpensive, relatively low-resolution gaze tracking apparatuses 20, the average number of navigation key presses may be higher but the system would still work. For instance, significant benefits can be gained with gaze tracking accuracy of approximately +/−0.3 to 0.5 degree, which is a low error requirement for gaze tracking systems. With this level of permissible error, the gaze tracking apparatus 20 may comprise an inexpensive video camera, many of which are known and becoming increasingly popular for use in computer systems.

The user input device 25 comprises an operator input device with an element sensitive to pressure, physical contact, or other manual control by a human operator. This is referred to as "manual" input that "mechanically" actuates the user input device 25, in contrast to natural look input from the gaze tracking apparatus 20. As an example, the user input device 25 may comprise one or more of the following: a computer keyboard, a mouse, "track-ball", a foot-switch or trigger, pressure-sensitive transducer stick such as the IBM TRACKPOINT® product, tongue pointer, stylus/tablet, touchscreen, and/or any other mechanically controlled device.

In the particular embodiment illustrated in FIG. 1, a keyboard 40, a combined activation and selection key 45, and navigation keys 50 are shown. Navigation keys comprise, for example, up key 55, down key 60, right key 65, and left key 70. Additional navigation keys may be provided for other directions such as a diagonal direction.

Although the software programming associated with the user input device 25 may be included with the user input device 25, the particular example of FIG. 1 shows the necessary input device software implemented in the user input module 50, described below. The user input module 50 may be included solely in the computer 15, the user input device 25, or a combination of the two, depending upon the particular application.

The display 30 provides an electronic medium for optically presenting text and graphics to the operator. The display 30 may be implemented by any suitable computer display with sufficient ability to depict graphical images including an indicator or other method of highlighting an object. For instance, the display 30 may employ a cathode ray tube, liquid crystal diode screen, light emitting diode screen, or any other suitable video apparatus. The display 30 can also be overlaid with a touch sensitive surface operated by finger or stylus. The images of the display 30 are determined by signals from the video module 55, described below. The display 30 may also be referred to by other names, such as video display, video screen, display screen, video monitor, display monitor, etc. The displayed indicator may comprise an arrow, bracket, short line, dot, cross-hair, a box, or any other image suitable for selecting or highlighting a target, positioning an insertion point (caret) for text or graphics, etc.

The computer 15 comprises one or more application programs 60, a user input module 50, a gaze tracking module 35, system 10, and a video module 55. The computer 15 may be a new machine, or one selected from any number of different products such as a known personal computer, computer workstation, mainframe computer, or another suitable digital data processing device. As an example, the computer 15 may be an IBM THINKPAD® computer. Although such a computer clearly includes a number of other components in addition those of FIG. 1, these components are omitted from FIG. 1 for ease of illustration.

The video module 55 comprises a product that generates video signals representing images. These signals are compatible with the display 30 and cause the display 30 to show the corresponding images. The video module 55 may be provided by hardware, software, or a combination. As a more specific example, the video module 55 may be a video display card, such as an SVGA card.

The application programs 60 comprise various programs running on the computer 15, and requiring operator input from time to time. This input may comprise text (entered via the keyboard 40) as well as positional and target selection information (entered using 45, which in this embodiment is both the activation and selection key, as well as navigation keys 55, 60, 65, 70). The positional information positions an indicator relative to or otherwise highlights images supplied by the application program. The target selection information selects one or more targets on the displayed screen image identified by the gaze position at the moment the operator performs an operation such as pressing the activation key 45. Examples of application programs 60 include commercially available programs such as database programs, word processing, financial software, computer aided design, etc.

The user input module 50 comprises a software module configured to receive and interpret signals from the user input device 25. As a specific example, the user input module 50 may include a keyboard driver that receives electrical signals from the navigation keys 75 and provides an x-y output for moving an indicator on display 30. Similarly, the gaze tracking module 35 comprises a software module configured to receive and interpret signals from the gaze tracking apparatus 20. As a specific example, the gaze tracking module 35 may include a program that receives electrical signals from the gaze tracking apparatus 20 and provides an x-y output representing a point where the operator is calculated to be gazing, called the "gaze position".

System 10 serves to integrate manual operator input (from the user input module 50 and user input device 25) with eye gaze input (from the gaze tracking apparatus 20 and gaze tracking module 35). System 10 applies certain criteria to input from the gaze tracking apparatus 20 and user input device 25 to determine how objects are shown on the display 30.

Figure 2:
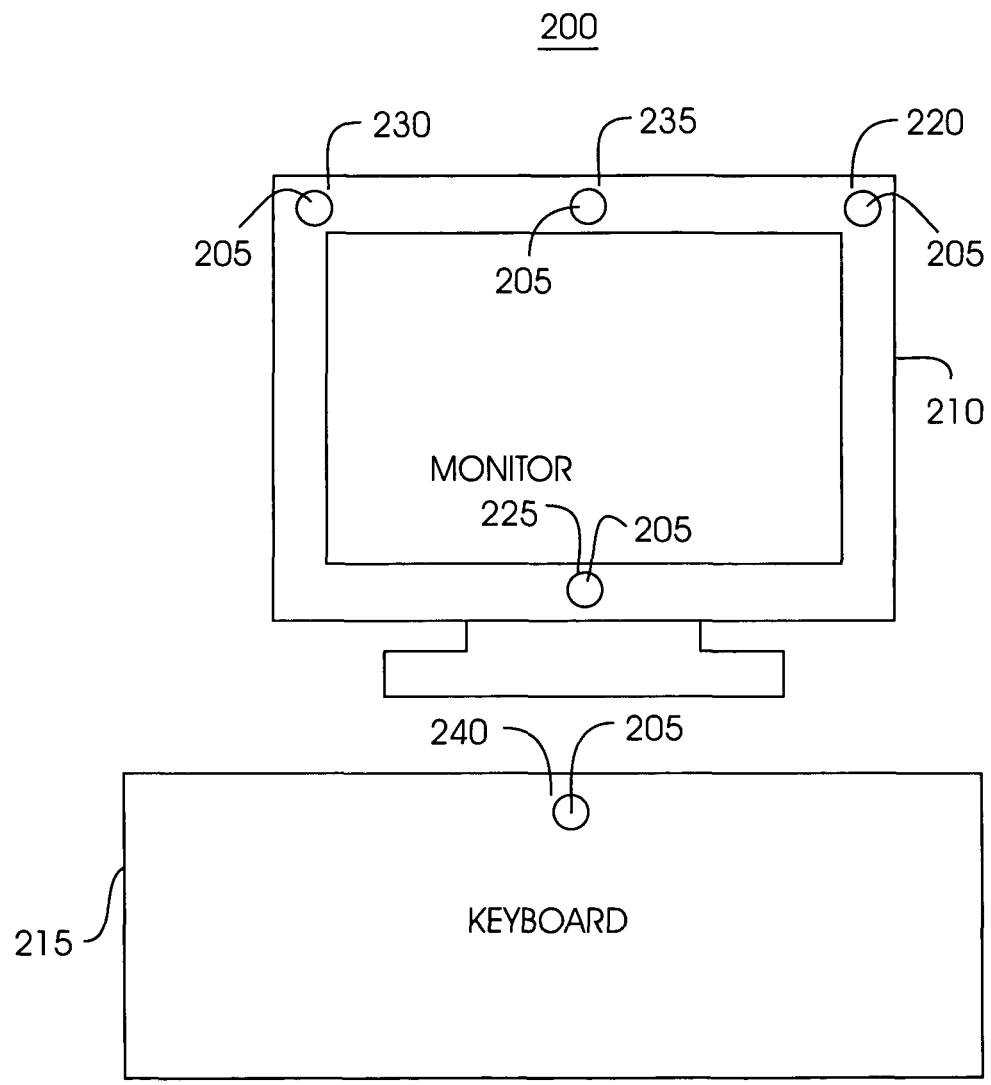
FIG. 2 is diagram of an exemplary computer system illustrating the placement of an eye gaze apparatus for capturing a gaze position for the target object selection system of FIG. 1.

FIG. 2 illustrates an exemplary computer system 200 in which the integrated gaze/manual control system 100 can be used. A small camera 205 functions as the gaze tracking apparatus 20. A monitor 210 functions as display 30. A keyboard 215 functions as the input device 25. In an embodiment, camera 205 is placed in position 220. In further embodiments, camera 205 may be placed in position 225, 230, 235, or any other position on monitor 210 from which the gaze position of the user may be determined. In yet another embodiment, additional cameras such as camera 205 may be placed in position 225, 230, 235, or any other position on monitor 210 by which the gaze position of the user may be determined.

In a further embodiment, camera 205 may be placed in position 240 on keyboard 215 or any other position on keyboard 215 by which the gaze position of the user may be determined. Furthermore, camera 205 in position 240 may be the only device used by the gaze tracking module or camera 205 in position 240 may be used in conjunction with additional cameras such as camera 205 in other positions such as position 225, 230, 235 on monitor 210.

Figure 3:
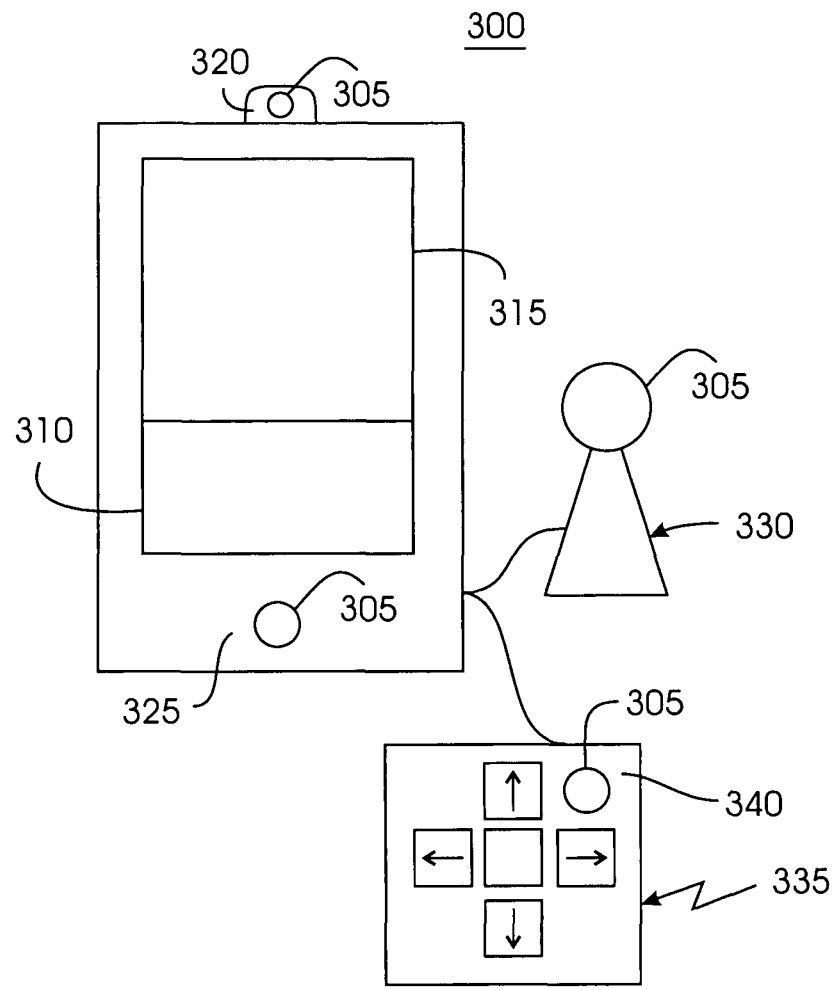
FIG. 3 is a diagram of an exemplary personal digital assistant illustrating the placement of an eye gaze apparatus for capturing a gaze position for the target object selection system of FIG. 1.

FIG. 3 illustrates an exemplary device such as a personal digital assistant 300 in which the integrated gaze/manual control system 100 can be used. A small camera 305 functions as the gaze tracking apparatus 20. A virtual keyboard 310 functions as the input device 25. A screen 315 functions as display 30. In an embodiment, camera 305 is placed in position 320. In further embodiments, camera 305 may be placed in position 325 or any other position on the personal digital assistant by which the gaze position of the user may be determined.

In another embodiment, camera 305 may be provided as an accessory 330 to the personal digital assistant 300 in a separate housing and placed by the user in a position that best determines the gaze position of the user. In a further embodiment, the activation key 45 and navigation keys 75 may be provided as an accessory to the personal digital assistant 300 in a separate housing as illustrated by user input device 335. In a similar fashion, user input device 340 can be provided as an accessory to any system in which a user selects objects on a graphical user interface. In a further embodiment, user input device 340 comprises camera 305 in a location such as, for example, location 340.

Interacting with a target is not limited to the use of the activation key 45 and navigation keys 50. In one embodiment, the integrated gaze/manual control system 100 captures a gesture from the user such as, for example, moving a finger. A device that captures the gestures of the user functions as the user input device 25. Such a device may be, for example, an IR device. Different gestures can be interpreted by system 10 as activation, selection or navigation. In a further embodiment, the user input device 25 is a microphone by which a user may provide voice commands for activation and navigation. Any method by which the user can communicate to the integrated gaze/manual control system 100 the simple commands of activation, selection and navigation may be used by the system 10 to select and activate targets on a graphical user interface.

Figure 4:
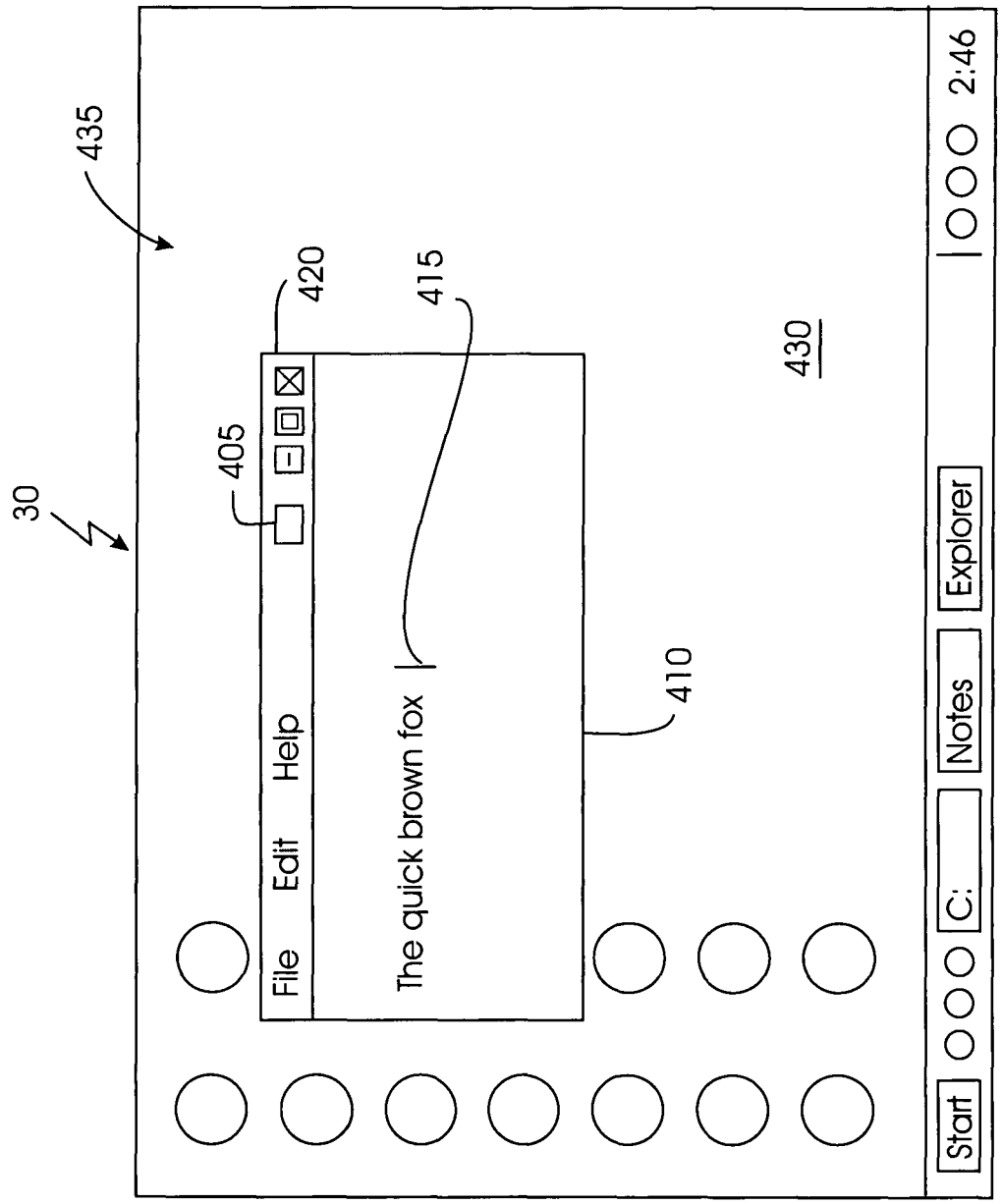
FIG. 4 is a diagram of a display illustrating graphical user interface objects that may be selected by the target object selection system of FIG. 1.

System 10 operates in object space rather than geometry space. For example, display 30 is defined as a set of objects and every spot on display 30 belongs to a target. FIG. 4 illustrates an exemplary screen shot of display 30 with several targets: a button 405, a text block 410, an insertion point 415 (also referenced herein as caret 415), a menu item 420, and a desktop 430, referenced collectively as targets 435.

The user looks in a natural manner (a natural look) at an object such as button 405 and presses a key such as the activation key 45. Using input from the gaze tracking module 35, system 10 determines which of the targets 435 is the desired target and highlights the desired target, button 405. Button 405 may be selected or highlighted by any number of methods such as, for example, placing an indicator on button 405, placing a box around button 405, changing the color of button 405, placing a color around button 405, etc.

If more than one of the targets 435 is a probable target, system 10 highlights the most probable target or targets. The user can select one of the other highlighted targets 435 if another object is the desired target object by using navigation keys 75 to move the indicator over one of the other targets 435. The user activates the object by pressing key 45 again.

Figure 5:
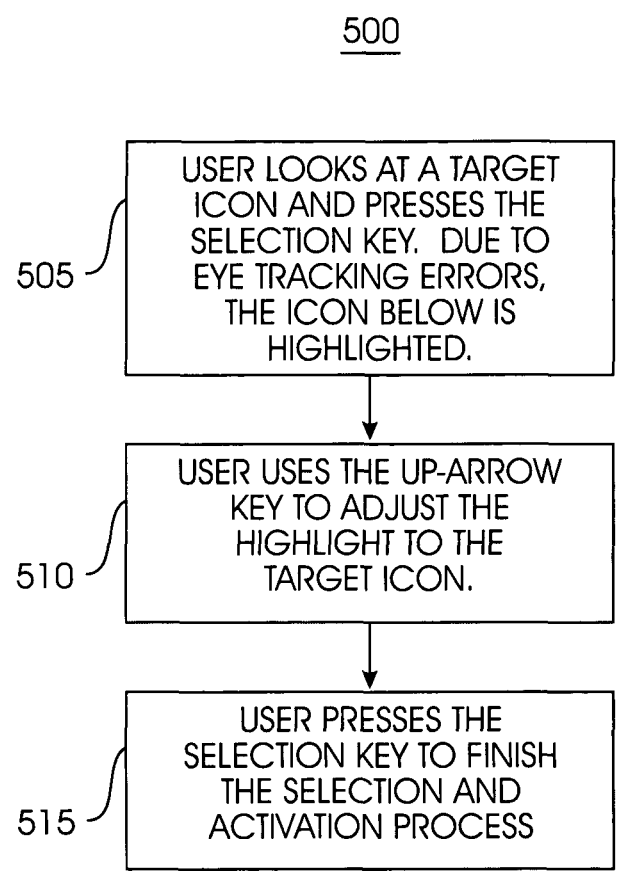
FIG. 5 is a high level flow chart illustrating the selection of graphical user interface objects by the target object selection system of FIG. 1.

FIG. 5 is a high level flow chart illustrating a method 500 for selecting graphical user interface objects by the target object selection system 10 of FIG. 1. At step 505, a user looks, rather than stares, at a target icon on the screen, and presses the selection key. Due to eye tracking errors, another adjacent icon, for example, the icon below the target icon is selected, e.g., highlighted. At step 510, the user uses the UP arrow key (or another key) to adjust the select (or highlight in this example) to the target icon. At step 515, once the target icon is selected, the user presses the key again to complete the interaction process.

In one embodiment, while the user is holding down, for example, the control key, the user momentarily presses a key such as the tab key. The most probable target is further highlighted. The user releases the control key to activate the target. If multiple targets have been highlighted, system 10 provides the user with an option to select one of the multiple targets, such as by a scroll down list. The user could, for example, holds down the control key and press the tab key to cycle through the various targets. When cycling, the currently active target is highlighted in a manner different from the other multiple targets. The currently highlighted target is activated when the control key is released.

In an embodiment, system 10 presents a menu representing the targets instead of the actual graphical representation of the targets. The user may then cycle through the list of targets on the menu to select the desired target object. In an embodiment, system 10 provides an option on the menu (i.e., an "exit" option) by which the user can choose to not select any of the targets presented on the menu.

A gaze position is assigned to one of the targets 430 according to a probabilistic model of system 10. Any number of probabilistic models may be used by system 10. A simple gaze assignment algorithm attaches the gaze position to an object underneath the gaze position. A more sophisticated method utilizes a likelihood model for each object underneath the gaze position. The likelihood, for example, can be a two dimensional Gaussian model:

$$\frac{1}{2\pi\sigma^2} \exp\left\{ -\frac{(x_g - x_o)^2 + (y_g - y_o)^2}{2\sigma^2} \right\}$$

where $(x_g, y_g)$ is the coordinate of the gaze position and $(x_o, y_o)$ is the coordinate of an object O. The standard deviation, σ, is determined by the size of the object, the distance from the object to its neighbors, the type of object, and situation in which the object is located. For example, desktop 430 has a distribution model with a greater standard deviation than a packed array of buttons such as button 405.

Figure 6:
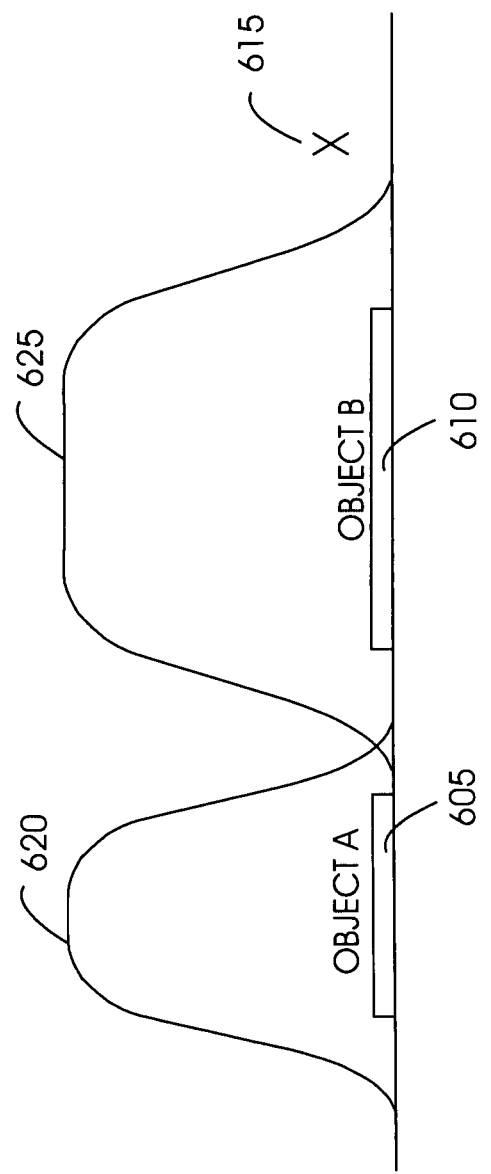
FIG. 6 is a probability diagram illustrating a probability determined by the target object selection system of FIG. 1 for graphical user interface objects on a display.

FIG. 6 illustrates in two dimensions the probability that an object A, 605, or an object B, 610, are the intended target of a gaze position 615. According to this example, the probability 620 of object A, 605, as the intended target is less than the probability 625 of object B, 610. However, system 10 operates in object space and has knowledge regarding the functions and current state of the object A, 605, and the object B, 610. For example, object A, 610 may be the text block 410 with the insertion point 415 at the end of a text field in the text block 410.

The object B, 610, may be a portion of the desktop 430. System 10 recognizes that even though object B, 610, has a greater probability than object A, 605, the user is currently entering text. Consequently, object A, 605, representing text block 410 is selected as the target and highlighted by system 10. System 10 uses knowledge regarding the functions and current state of each object on the graphical user interface to behave intelligently and offer flexibility to the user.

The use of a state of an object by system 10 is illustrated by the simple example of FIG. 7, a typical application form 700 that a user completes on a webpage on the Internet. System 10 uses the natural order of the items to be completed as well as the current state of application form 700 while it is being completed to improve the reliability of the probabilistic models used by system 10.

Applications such as application form 700 typically have certain properties that can be leveraged in the probabilistic model. For example, forms typically have a natural order in which the fields in the form are to be completed. Natural order is commonly used in conjunction with the tab key to navigate within the form. Sometimes this order is determined directly by the placement of items in the form, and other times it can be coded by the form developer. If elements in the form are numbered 1 to n and the user is currently modifying field k on the form, then the probabilistic model favors the form element at k+1. For example, a user is completing a city field 705. The next likely field on application 700 is then a state field 710. After completing the city field 705, the user can naturally look at the state field 710 and press the activation key 45.

System 10 selects the state field 710 as the most probable field even in instances where many buttons cluster around the state field 710. Forms typically have a "natural order", wherein many GUI tools allow the form elements to be actually numbered in the order they should be tabbed through. As an example, if there are 10 form elements, and form elements 1 through 5 are filled in, the idea is to bias 6. If additional information is available, such as whether the form field is optional or required, then this information could be fed into a more generic model. Likewise, history could be fed into this model as well. For example, if a person typically fills out a form in different order than the natural one, then this behavior might be learnable.

Further information may be coded into a form that can be used by system 10 in a similar way. For example, forms often have optional and required elements. A form is considered complete (i.e., ready to be processed) once all of the required elements have been completed. System 10 uses this information to further inform the probabilistic model, for example, by favoring a form element that is required over a form element that is optional.

System 10 uses state information to enhance the information available to the probabilistic model, thus improving the accuracy of system 10 in selecting the most probable target. For example, if a web page is currently loading in a web browser, a "stop" button is likely to be a desired target if the user is naturally looking in the area of the "stop" button and a "reload button". If the page is not currently loading, the "reload" button is more likely to be a desired target than the "stop" button.

Figure 8A:
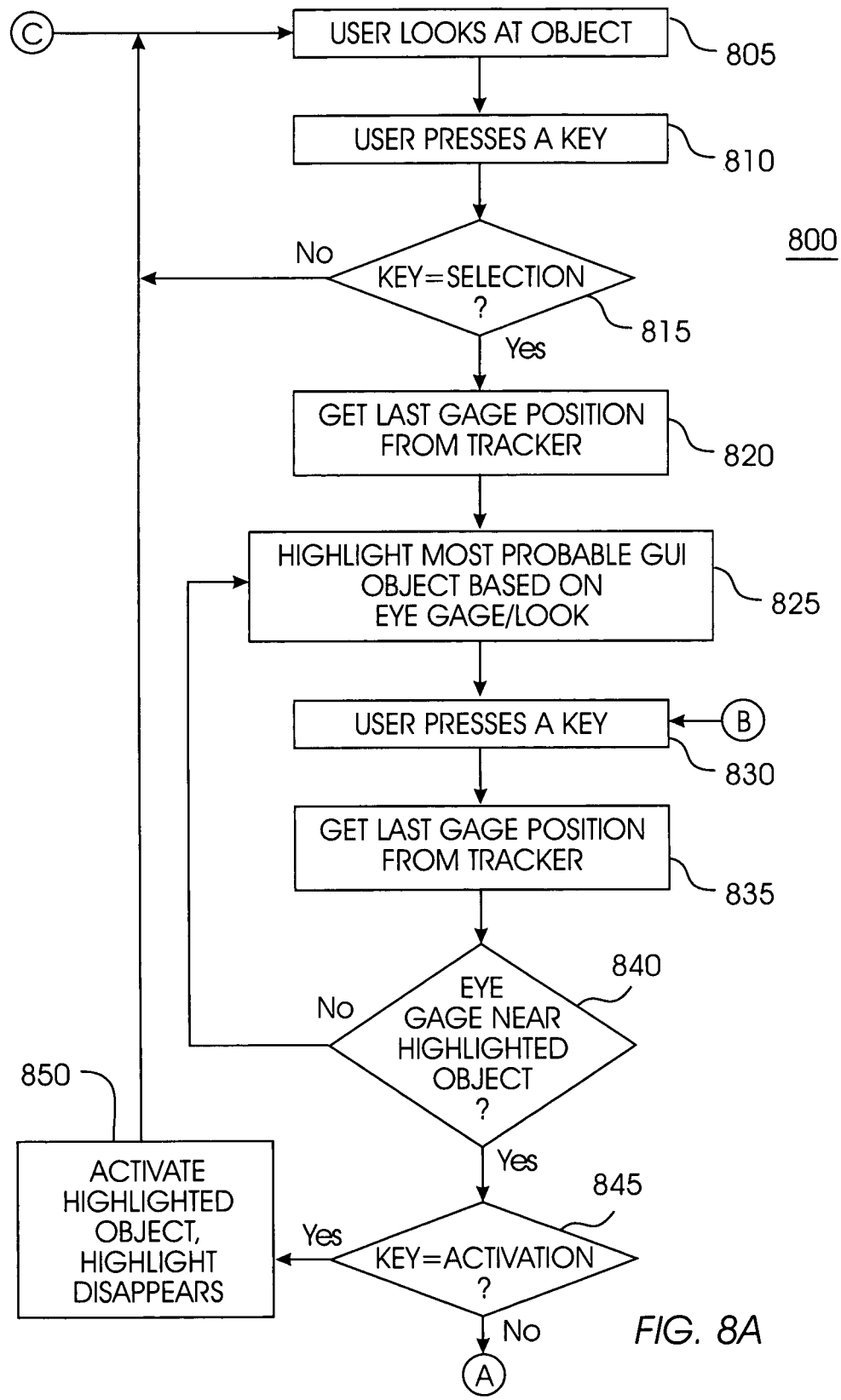
FIG. 8 is a process flow chart illustrating a method of the target object selection system of FIG. 1 in selecting a target on a display.
Figure 8B:
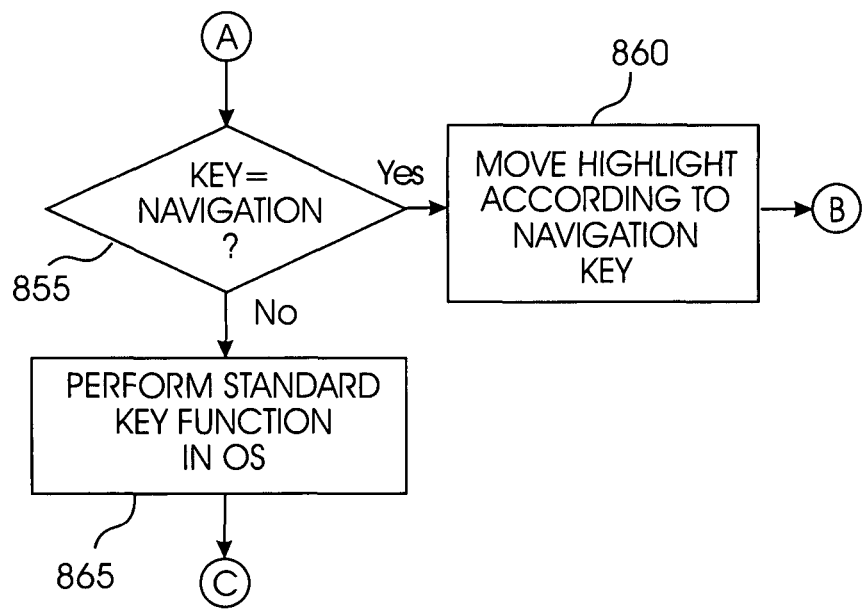

A process flow chart illustrating a method 800 of system 10 is illustrated in FIG. 8. Throughout method 800, system 10 is continually tracking the gaze position of the user. This gaze position is only used, however, when the user presses the selection key on the keyboard. Method 800 describes a process of using the selection and navigation keys to control how eye gaze is used for highlighting and selecting GUI objects. At a high level, the basic flow in FIG. 8 includes the following steps: (1) looking at a GUI object; (2) pressing the selection key to highlight it; (3) optionally using the navigation keys to adjust the highlight; and (4) pressing the activation key to activate the highlighted object. These steps will now be examined in more detail.

At step 805, the user looks at the target object, and then presses a key at step 810. At step 815, method 800 inquires if the key that has been pressed is the pre-assigned selection key. If it is not, then method 800 returns to step 805 and follows the user's look and gaze.

If, on the other hand, the key that has been pressed is the selection key, method 800 acquires the user's last gaze position from the eye gaze tracker at step 820. At step 825, this eye gaze position is used by system 10 to highlight the GUI object that is the most probable to have been selected by the user. System 10 uses its probability model over selectable GUI objects to help select the most probable object.

After the user presses another key at step 830, system 10 acquires the last gaze position from the tracker at step 835, and inquires at step 840 if the eye gaze is close to the highlighted object. If it is not, method 800 returns to step 825 and proceeds as described earlier. If the user has looked away from the highlighted object by the time of the second key press, then they probably want to move on to select a different GUI object.

If, however, method 800 determines at step 840 that the eye gaze is sufficiently close to the highlighted object, it inquires at step 845 if the key pressed at step 830 is the activation key. If it is, system 10 activates the highlighted object and the highlight is removed, at step 850. Method 800 then returns to step 805, and proceeds as described earlier.

If method 800 determines at decision step 845 that the pressed key is not the activation key, then method 800 inquires at decision step 855 if the pressed key is a navigation key. If it is not, then system 10 performs the normal operating system function for that key, and returns to step 805, as described earlier.

If method 800 determines at decision step 855 that the pressed key is a navigation key, then system 10 moves the selection highlight according to the navigation key instruction, at step 860, and returns to step 830 as described earlier.

In one embodiment, system 10 allows the user to use any set of five or more keys on a keyboard to navigate to the next most probable target. In a further embodiment, an indicator such as an arrow is placed over the most probable target. Alternatively, the most probable target may be indicated by any number of methods such as by placing a box around the most probable target object, highlighting the most probable target object, etc. The set of five or more keys can then be used to move the indicator over the desired target or otherwise adjust the indicator placement. The set of five or more keys provide functionality in addition to the activation and selection key 45 and the navigation keys 55, 60, 65, and 70. It is also possible to use a set of 9 keys (including the four arrow keys: up down, left, and right), so the user could move the highlight diagonally.

Figure 9A:
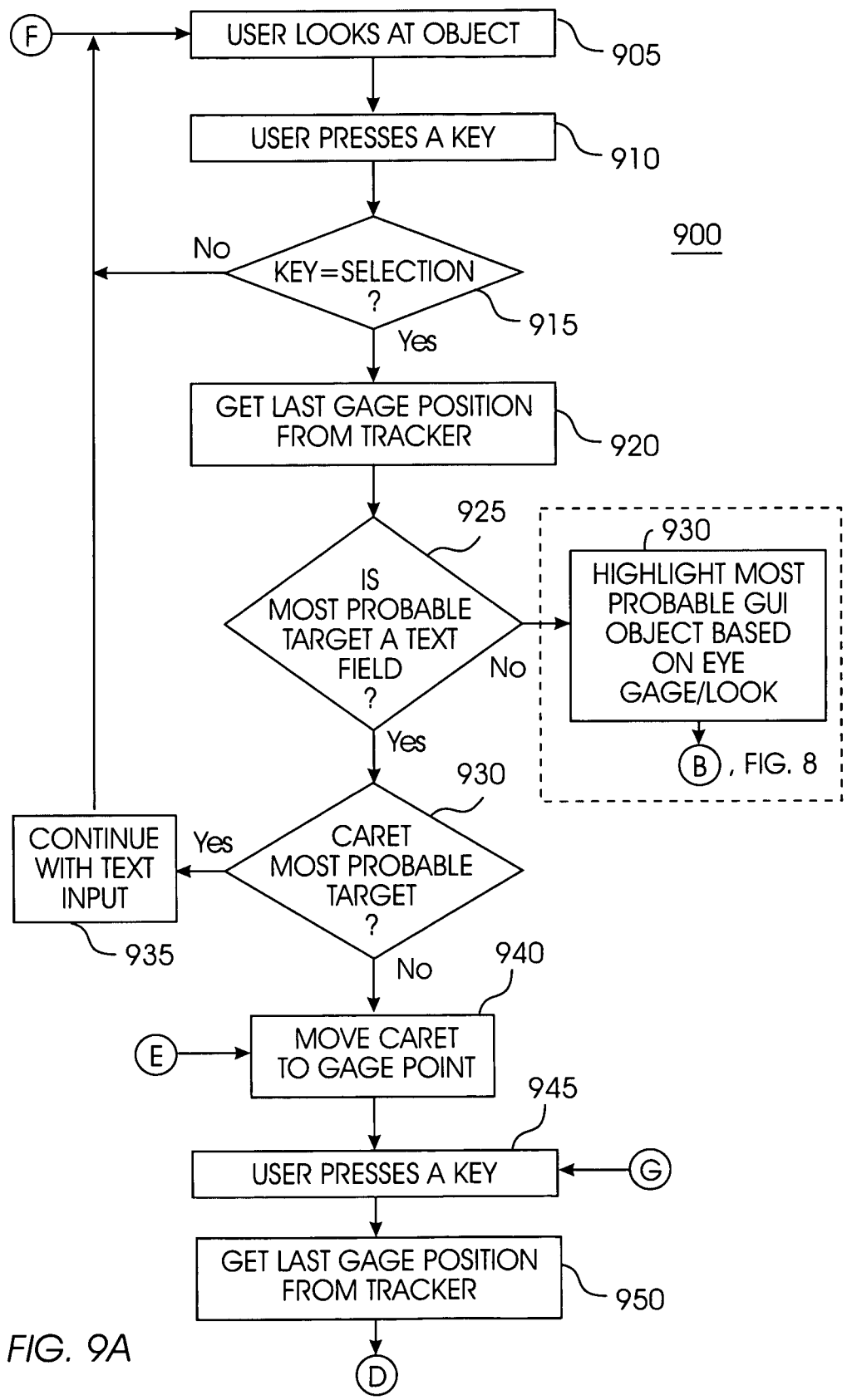
FIG. 9 is a process flow chart illustrating a method of using the target object selection system of FIG. 1 that involves moving the caret position in a block of text.
Figure 9B:
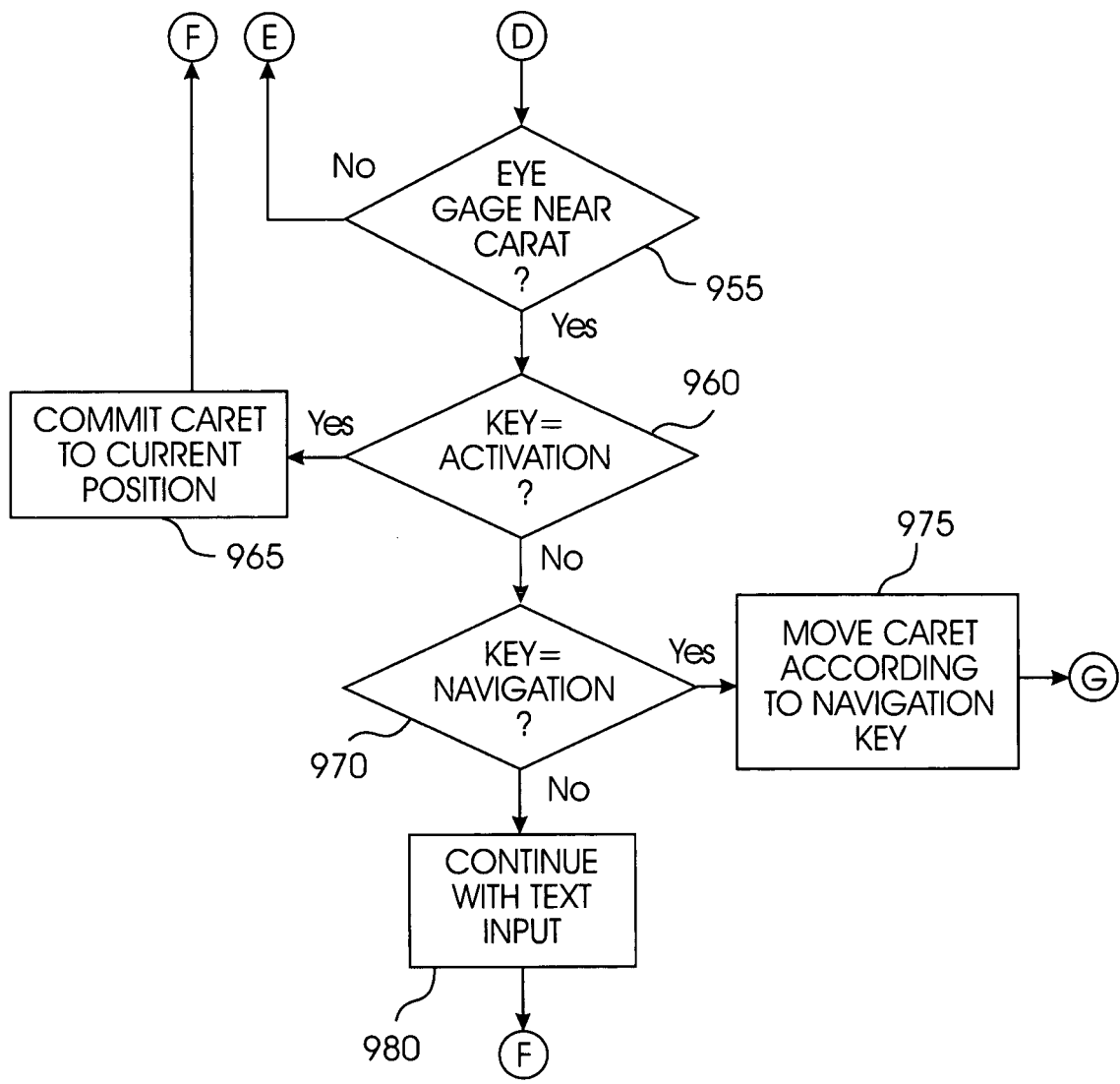

A method 900 of system 10, illustrated in FIG. 9, is a refinement of the basic method when the selected object is a text field. At step 905, the user looks at the target object, and then presses a key at step 910. At step 915, method 900 inquires if the key that has been pressed is the pre-assigned selection key. If it is not, then method 900 returns to step 905 and follows the user's look and gaze.

If, on the other hand, the key that has been pressed is the selection key, method 900 acquires the user's last gaze position from the eye gaze tracker at step 920 and computes the most probable GUI object in accordance with system 10's probability model. Method 900 then inquires at decision step 925 whether the most probable target is a text field. If it is not, system 10 highlights the most probable GUI object based on the user's eye gaze, as described earlier in connection with FIG. 8, starting at step 830.

If however, method 900 determines at decision step 925 that the most probable target is a text field, method 900 determines at decision step 930 if the most probable object is the caret 415 when a key on the keyboard 1000 is pressed. If the caret 415 is the most probable target, the user is in the process of entering text in text box 410, and system 10 continues with text input at step 935 and the character pressed by the user is added to the text string at the point of insertion, caret 415.

If method 900 determines at decision step 930 that the caret 415 is not the most probable object, then system 10 moves the caret 415 to the gaze point at step 940. When the user presses another key at step 945, method 900 acquires the last position from the tracker at step 950, and proceeds to decision step 955.

At decision step 955, method 900 inquires if the eye gaze is in proximity to the caret 415. If it not, method 900 returns to step 940 and proceeds as described earlier. If, on the other hand, method 900 determines at decision step 955 that the eye gaze is in proximity to the caret 415, method 900 inquires at decision step 960 if the key that has been pressed at step 945 is the activation key. If it is, then system 10 commits the caret 415 to its current position.

Otherwise, method 900 inquires at decision step 970 if the pressed key is a navigation key. If it is, then system 10 moves the caret 415 according to the navigation key at step 975, and then proceeds to step 945 as described before.

If, however, method 900 determines at decision step 970 that the pressed key is not a navigation key, it proceeds to step 980 where system 10 continues with the text input at step 980, and proceeds to 905 as described earlier.

Figure 10:
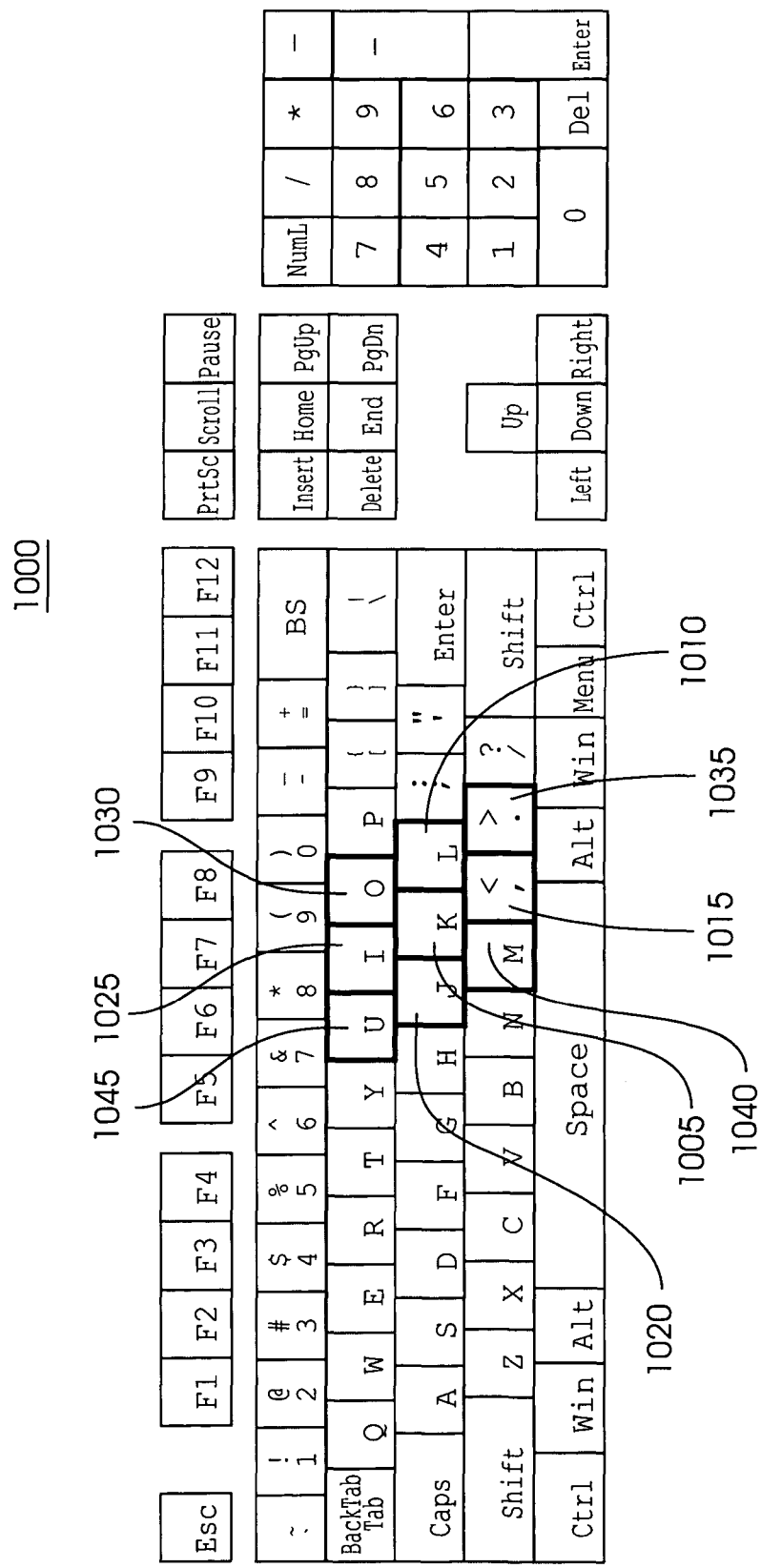
FIG. 10 is a diagram of an exemplary keyboard illustrating the method of FIG. 9.

FIG. 10 illustrates on a typical keyboard 1000 the use of any set of five or more keys by system 10 to identify and activate a target. For example, the user may press a "K" key 1005 to select a target on the display 30. The "K" key 1005 becomes the anchor key. In an embodiment, a symbol or other indicator appears on the most probable target. Alternatively, the most probable target is highlighted in some other fashion as previously discussed. The keys around the "K" key 1005 move the indicator in a direction corresponding to the direction of the keys from the "K" key 1005.

The user may now press the "L" key 1010 to move the indicator to the right, highlighting the target to the right of the currently highlighted object. Pressing the "," key 1015 moves the indicator down. Pressing the "J" key 1020 moves the indicator left. Pressing the "I" key 1025 moves the indicator up. Furthermore, pressing the "O" key 1030 moves the indicator diagonally to the upper right. Pressing the "." key moves the indicator to the lower right. Pressing the "M" key 1040 moves the indicator to the lower left. Pressing the "U" key moves the indicator to the upper right. A second press of the "K" key 1005 (the anchor key) by the user activates the highlighted object, causing the highlighted object to perform its designated function.

In a further embodiment, system 10 allows keys used by both the right and left hands for selection, activation and navigation. For example, the left hand can press the control or "alt" key to select a target. The right hand can use other keys to navigate to alternate targets and activate the target using, for example, the enter key.

Figure 11B:
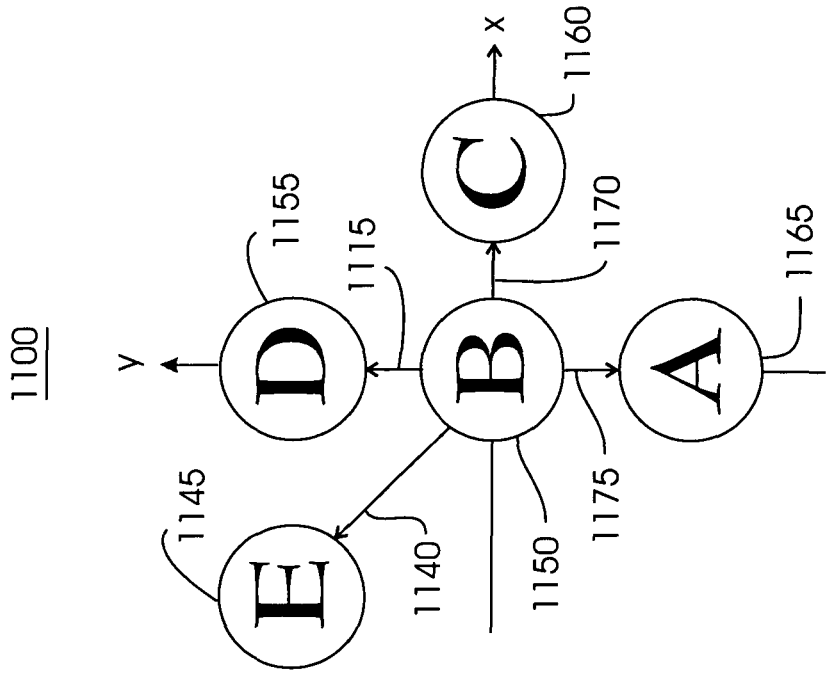
FIG. 11 is a diagram illustrating selection of a target using involuntary movements by a user's eye after an initial target has been selected.
Figure 11A:
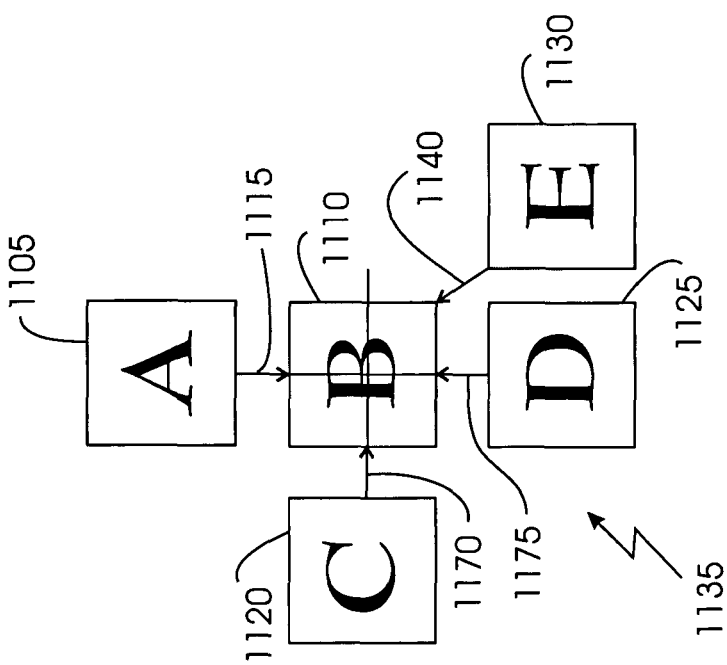

In an embodiment illustrated by FIG. 11 (FIGS. 11A, 11B), system 10 uses eye gaze feedback rather than the navigation keys 50 to select a target other than the highlighted target. For example, a user looks at object A, 1105, while pressing the selection and activation key 45. Due to the natural inaccuracies of currently available gaze tracking apparatus, system 10 may select object B, 1110, rather than object A, 1105, as the most probable target. System 10 then highlights object B, 1110. The user is looking at object A, 1105, expecting system 10 to highlight object A, 1105. When the user notices that item B, 1110, is highlighted instead, the user exhibits an involuntary saccade from item A, 1105, to item B, 1110. This saccade may be brief, but it is detectable by the gaze tracking module 35.

System 10 detects the saccade and uses it to quickly highlight the desired target. The saccade can be represented as a two dimensional saccade vector 1115 from the desired choice (item A, 1105) to the initial choice (item B, 1110). System 10 determines that item A, 1105, is the desired target, removes highlighting from item B, 1110, and highlights item A, 1105.

In a further embodiment, system 10 creates a probability model 900 of saccades under different scenarios using a two dimensional layout of display 30, as illustrated by FIG. 11B. Immediately prior to highlighting item B, 1110, system 10 creates probability models in a two dimensional (x, y) "saccade" space 900 around item B, 1110, as shown in FIG. 11B. System 10 places the item to be highlighted, item B, 1110, in the center of the "saccade" space 1100. All other probable targets within a predetermined gaze diameter are placed around the item to be highlighted. Other probable targets in this example are item A, 1105, item C, 1120, item D 1125, and item E, 1130, collectively referenced as probable targets 1135.

In the "saccade" space 1100, each of the probable targets 1130 are placed in the position to which the user's eye travels in an involuntary saccade from the desired target to the highlighted target. For example, if item E, 1115, is below and to the right of item B, 1105, on display 30, the saccade indicating that item E, 1115, is the desired target is a vector 1140 from item E, 1115, to item B, 1105, or on a diagonal to the upper right. Consequently, saccade E, 1145, is placed above and to the right of saccade B, 1150, in FIG. 11B. Saccade E, 1145, is at the tail of saccade vector 1140 rather than at the origin of saccade vector 1140. Similar placement is used for each of the other probable targets 1135: saccade D, 1155, is placed above saccade B, 1150; saccade C, 1160, is placed to the right of saccade B, 1150; and saccade A, 1165, is placed below saccade B, 1150. The saccade vectors 1170, 1175 remain the same but the relative positions of the initial target (item B, 1105) and the other probable targets 1135 are reversed.

System 10 uses only saccades captured by the gaze tracking module 35 within a specified saccade time window after system 10 highlights the most probable target. In an embodiment, the saccade time window is approximately 200 ms. Captured saccades are used by system 10 that fit a predetermined probability distribution. When a captured saccade occurs during the saccade time window and exhibits the maximum probability within the region indicated by the saccade, system 10 removes highlighting from the initial target and highlights the target that the saccade indicates.

Figure 12:
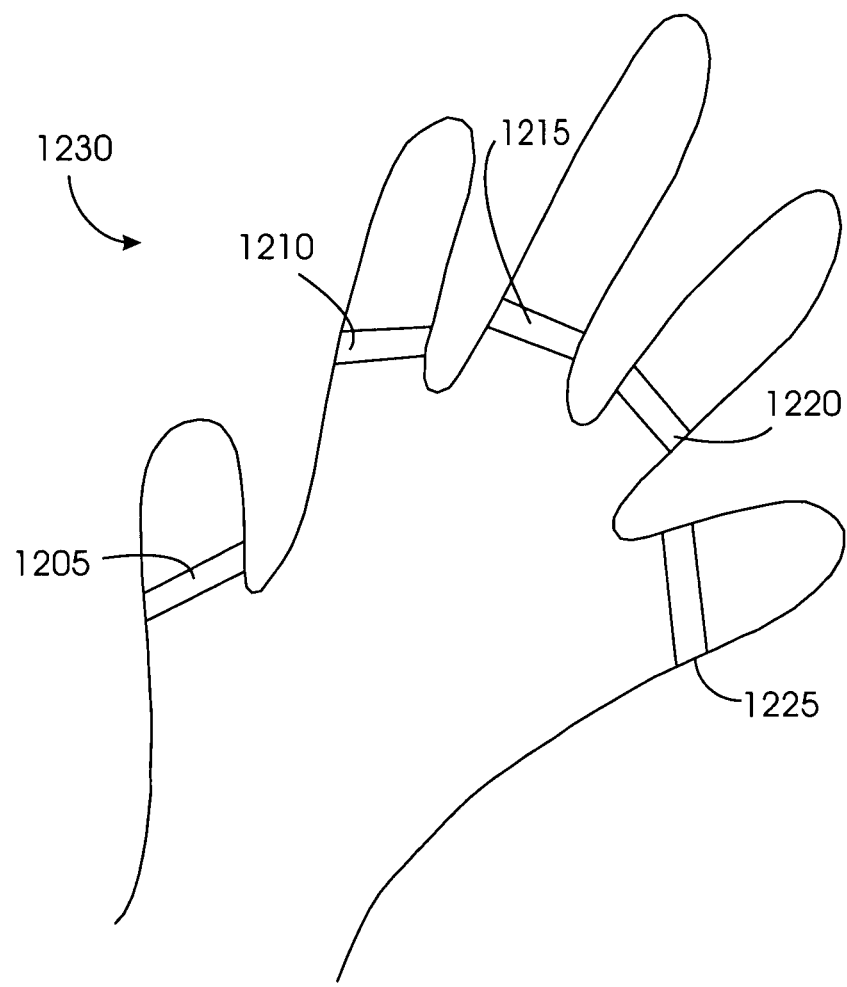
FIG. 12 is a diagram illustrating an embodiment of the target object selection system of FIG. 1 in which selection and navigation functions are performed by moving a finger.

Because system 10 does not require input from a pointing device, system 10 may be implemented in a variety of applications that capture a signal from a user. For example, a user may perform the function of the activation key 45 and the functions of the navigation keys 50 by wearing a set of movement-monitoring devices on the fingers of a hand, as illustrated by FIG. 12. FIG. 12 shows the movement monitoring devices as rings such as ring 1205, 1210, 1215, 1220, 1225, referenced collectively as rings 1230. In an embodiment, the function of the rings 1230 may be provided by a glove. For example, ring 1205 functions as the activation key 45 and rings 1210, 1215, 1220, and 1225 function as the navigation keys.

It is to be understood that the specific embodiments of the invention that have been described are merely illustrative of certain applications of the principle of the present invention. Numerous modifications may be made to the system and method for selecting a target object using eye gaze and a selection key described herein without departing from the spirit and scope of the present invention.

What is claimed is:

1. A method for selecting a target object from a plurality of objects, the method comprising:
   displaying a plurality of objects on a display;
   tracking a gaze position of a natural look of a user while viewing the display, wherein the natural look is directed to a general area on the display;
   monitoring for a press of a manual selection key;
   determining, based on the monitoring, that the manual selection key has been selected;
   obtaining, based on the manual selection key being selected, a gaze position of the natural look of the user that has occurred prior to the manual selection key having been selected;
   assigning, based on the manual selection key having been selected, the gaze position that has been obtained to at least one object within the general area of the display based on a probabilistic model applied to the gaze position and at least one of a function of the object and a current state of the object, wherein the probabilistic model is applied based on the manual selection key having been selected;
   identifying, based on the assigning, a set of objects from the plurality of objects, wherein each of the set of objects are within a given gaze diameter from the at least one object;
   creating, after the set of objects has been identified, a probability model of saccades comprising a two-dimensional saccade space surrounding the at least one object, wherein the at least one object is placed in a center of the two-dimensional saccade space, and wherein each of the set of objects are placed at position in the two-dimensional saccade space associated with a vector representing a direction of travel of an eye of the user from the object in the set of additional objects to the at least one object;
   detecting at least one saccade performed by the user;
   identifying the vector in the two-dimensional saccade space corresponding to the at least one saccade;
   determining that the gaze position has been incorrectly assigned to the at least one object in response to detecting the at least one saccade;
   selecting, based on the determining that the gaze position has been incorrectly assigned, the object in the set of objects associated with the vector on the display, wherein the selecting indicates the gaze position of the user; and
   assigning the gaze position of the user to the object in the set of objects that has been selected.

2. The method of claim 1, wherein the probabilistic model comprises a history of a graphical user interface object.

3. The method of claim 1, wherein the object in the set of objects is a graphical user interface object.

4. The method of claim 1, wherein selecting the object in the set of objects comprises capturing the position of the natural look upon a user pressing the manual selection key.

5. The method of claim 1, wherein selecting the object in the set of objects comprises highlighting the object.

6. The method of claim 5, wherein highlighting the object is using a bounding box.

7. The method of claim 5, wherein highlighting the object is implemented by changing a color of the object.

8. The method of claim 5, wherein highlighting the object is implemented by placing a cursor adjacent to the object.

9. The method of claim 5, wherein highlighting the object is implemented by pointing an arrow to the object.

10. The method of claim 1, wherein the at least one saccade is detected based on highlighting the at least one object.

11. The method of claim 10, further comprising highlighting the wherein the two-dimensional saccade space is created immediately prior to highlighting the at least one object.

12. The method of claim 1, wherein the object in the set of objects is selected based on detecting a combined press of two keys.

13. The method of claim 12, wherein the two keys are a control key and a tab key.

14. The method of claim 13, wherein the selected object is changed based on a navigation through the plurality of objects using the tab key.

15. The method of claim 13, wherein the object is activated based on releasing the control key.

16. The method of claim 1, wherein the manual selection key is a dedicated key on a keyboard.

17. The method of claim 1, wherein the manual selection key is a user-defined key on a keyboard.

18. The method of claim 1, wherein the manual selection key is any key on a keyboard.

19. The method of claim 1, further comprising:
   receiving, based on the selecting, an input from a navigation key, wherein the navigation key is different than the manual selection key;
   selecting, based on receiving the input from the navigation key, a new object on the display; and
   activating the new object that has been selected with an activation key.

20. The method of claim 19, wherein the activation key is a dedicated key on a keyboard.

21. The method of claim 19, wherein the activation key is a user-defined key on a keyboard.

22. The method of claim 19, wherein the activation key is any key on a keyboard.

23. The method of claim 1, further comprising:
   determining that the object includes a text field;

determining whether the position of the natural look is one of at and near a caret in the text field;

continuing with text entry based on the position of the natural look being one of at and near the caret in the text field; and moving the caret to the position of the natural look based on the position of the natural look failing to be one of at and near the caret in the text field.

24. The method of claim 1, wherein the probabilistic model is based on a set of coordinates associated with the gaze position, a set of coordinates associated with the object and a standard deviation that is based on at least one of a size of the object, a distance of the object to one or more neighbor objects, a type of the object, and an environment in which the object is located.

25. The method of claim 1, wherein the at least one saccade is detected within a given window of time after the at least one object has been assigned.

26. A pointing apparatus for selecting a target object from a plurality of objects, the pointing apparatus comprising:
a display for displaying a plurality of objects;
a gaze tracking module that tracks a gaze position of a natural look of a user while viewing the display, wherein the natural look is directed to a general area on the display;
a user input module that concurrently monitors for a press of a manual selection key;
the user input module further
determines, based on monitoring for a press of the manual selection key, that the manual selection key has been selected;
obtains, based on the manual selection key being selected, a gaze position of the natural look of the user that has occurred prior to the manual selection key having been selected;
assigns, based on the manual selection key having been selected, the gaze position that has been obtained to at least one object within the general area of the display based on a probabilistic model applied to the gaze position and at least one of a function of the object and a current state of the object, wherein the probabilistic model is applied based on the manual selection key having been selected;
identifies, based on the assigning, a set of objects from the plurality of objects, wherein each of the set of objects are within a given gaze diameter from the at least one object;
creates, after the set of objects has been identified, a probability model of saccades comprising a two-dimensional saccade space surrounding the at least one object, wherein the at least one object is placed in a center of the two-dimensional saccade space, and wherein each of the set of objects are placed at position in the two-dimensional saccade space associated with a vector representing a direction of travel of an eye of the user from the object in the set of additional objects to the at least one object;
detects at least one saccade performed by the user;
identifies the vector in the two-dimensional saccade space corresponding to the at least one saccade;
determines that the gaze position has been incorrectly assigned to the at least one object in response to detecting the at least one saccade;
selects, based on the determining that the gaze position has been incorrectly assigned, the object in the set of objects associated with the vector on the display, wherein the selecting indicates the gaze position of the user; and assigning the gaze position of the user to the object in the set of objects that has been selected.

27. The pointing apparatus of claim 26, wherein the probabilistic model comprises a history of a graphical user interface object.

28. The pointing apparatus of claim 26, wherein the object is a graphical user interface object.

29. The pointing apparatus of claim 26, wherein the user input module selects the object in the set of objects by capturing a position of the natural look upon the user pressing the manual selection key.

30. The pointing apparatus of claim 26, wherein the user input module further:
receives, based on selecting the object, an input from a navigation key, wherein the navigation key is different than the manual selection key;
selects, based on receiving the input from the navigation key, a new object on the display; and
activates the new object that has been selected with an activation key.

31. The pointing apparatus of claim 26, wherein the user input module further:
determines that the object includes a text field;
determines whether the position of the natural look is one of at and near a caret in the text field;
continues with text entry based on the position of the natural look being one of at and near the caret in the text field; and
moves the caret to the position of the natural look based on the position of the natural look failing to be one of at and near the caret in the text field.

32. The pointing apparatus of claim 26, wherein the probabilistic model is based on a set of coordinates associated with the gaze position, a set of coordinates associated with the object and a standard deviation that is based on at least one of a size of the object, a distance of the object to one or more neighbor objects, a type of the object, and an environment in which the object is located.

33. A computer program product for selecting a target object from a plurality of objects, the computer program product comprising:
a non-transitory storage medium readable by a processing circuit and storing instructions for execution by the processing circuit for performing a method comprising:
displaying a plurality of objects on a display;
tracking a gaze position of a natural look of a user while viewing the display, wherein the natural look is directed to a general area on the display;
monitoring for a press of a manual selection key;
obtaining, based on the manual selection key being selected, a gaze position of the natural look of the user that has occurred prior to the manual selection key having been selected;
selecting the target object based on a coincidence of the press of the manual selection key and a sensed user's natural look to a region proximate to the target object;
determining, based on the monitoring, that the manual selection key has been selected;
assigning, based on the manual selection key having been selected, the gaze position that has been obtained to at least one object within the general area of the display based on a probabilistic model applied to the gaze position and at least one of a function of the object and a current state of the object, wherein the probabilistic model is applied based on the manual selection key having been selected;

identifying, based on the assigning, a set of objects from the plurality of objects, wherein each of the set of objects are within a given gaze diameter from the at least one object;

creating, after the set of objects has been identified, a probability model of saccades comprising a two-dimensional saccade space surrounding the at least one object, wherein the at least one object is placed in a center of the two-dimensional saccade space, and wherein each of the set of objects are placed at position in the two-dimensional saccade space associated with a vector representing a direction of travel of an eye of the user from the object in the set of additional objects to the at least one object;

detecting at least one saccade performed by the user;

identifying the vector in the two-dimensional saccade space corresponding to the at least one saccade;

determining that the gaze position has been incorrectly assigned to the at least one object in response to detecting the at least one saccade;

selecting, based on the identifying, the object in the set of objects associated with the vector on the display, wherein the selecting indicates the gaze position of the user; and assigning the gaze position of the user to the object in the set of objects that has been selected.

34. The computer program product of claim 33, wherein selecting the object in the set of objects comprises capturing a position of the natural look upon the user pressing the manual selection key.

35. The computer program product of claim 33, wherein the probabilistic model comprises a history of a graphical user interface object.

36. The computer program product of claim 33, wherein the object is a graphical user interface object.

37. The computer program product of claim 33, wherein the method further comprises:

receiving, based on the selecting, an input from a navigation key, wherein the navigation key is different than the manual selection key;

selecting, based on receiving the input from the navigation key, a new object on the display; and activating the new object that has been selected with an activation key.

38. The computer program product of claim 33, wherein the method further comprises:

determining that the object includes a text field;

determining whether the position of the natural look is one of at and near a caret in the text field;

continuing with text entry based on the position of the natural look being one of at and near the caret in the text field; and moving the caret to the position of the natural look based on the position of the natural look failing to be one of at and near the caret in the text field.

39. The computer program product of claim 33, wherein the probabilistic model is based on a set of coordinates associated with the gaze position, a set of coordinates associated with the object and a standard deviation that is based on at least one of a size of the object, a distance of the object to one or more neighbor objects, a type of the object, and an environment in which the object is located.

* * * * *